United States Patent
Hayday et al.

(10) Patent No.: US 9,957,319 B2
(45) Date of Patent: May 1, 2018

(54) METHOD OF ISOLATING HUMAN ANTIBODIES

(71) Applicant: IMMUNOQURE AG, Dusseldorf (DE)

(72) Inventors: Adrian Hayday, Kent (GB); Kai Krohn, Samentaka (FI); Annamari Ranki, Helsinki (FI); Part Peterson, Tallinn (EE); Kai Kisand, Tartu (EE); Edward Stuart, Meerbusch (DE); Annalisa Macagno, Schlieren (CH)

(73) Assignee: ImmunoQure AG (DE)

( * ) Notice: Subject to any disclaimer, the term of this patent is extended or adjusted under 35 U.S.C. 154(b) by 334 days.

(21) Appl. No.: 14/368,749

(22) PCT Filed: Jan. 2, 2013

(86) PCT No.: PCT/EP2013/050026
§ 371 (c)(1),
(2) Date: Jun. 25, 2014

(87) PCT Pub. No.: WO2013/098420
PCT Pub. Date: Jul. 4, 2013

(65) Prior Publication Data
US 2014/0335098 A1 Nov. 13, 2014

Related U.S. Application Data

(60) Provisional application No. 61/580,837, filed on Dec. 28, 2011.

(30) Foreign Application Priority Data

Dec. 28, 2011 (EP) ..................... 11195952

(51) Int. Cl.
*C07K 16/24* (2006.01)
*C07K 16/06* (2006.01)
*C07K 16/18* (2006.01)
*C07K 16/00* (2006.01)
*G01N 33/569* (2006.01)
*A61K 39/395* (2006.01)
*A61K 45/06* (2006.01)
*C07K 16/42* (2006.01)
*G01N 33/68* (2006.01)
*A61K 39/00* (2006.01)

(52) U.S. Cl.
CPC ........ *C07K 16/244* (2013.01); *A61K 39/3955* (2013.01); *A61K 45/06* (2013.01); *C07K 16/00* (2013.01); *C07K 16/065* (2013.01); *C07K 16/18* (2013.01); *C07K 16/4241* (2013.01); *G01N 33/56972* (2013.01); *G01N 33/6869* (2013.01); *A61K 2039/505* (2013.01); *A61K 2039/507* (2013.01); *C07K 2317/14* (2013.01); *C07K 2317/21* (2013.01); *C07K 2317/33* (2013.01); *C07K 2317/76* (2013.01); *C07K 2317/92* (2013.01); *C12N 2501/599* (2013.01); *G01N 2333/54* (2013.01)

(58) Field of Classification Search
None
See application file for complete search history.

(56) References Cited

U.S. PATENT DOCUMENTS

| 6,309,636 B1 | 10/2001 | do Couto et al. | |
|---|---|---|---|
| 2003/0099649 A1 | 5/2003 | Jacobs et al. | |
| 2009/0130120 A1* | 5/2009 | Kauvar | C07K 16/1027 424/147.1 |

FOREIGN PATENT DOCUMENTS

| WO | WO 2004/076677 | 9/2004 |
|---|---|---|
| WO | WO 2007/068758 | 6/2007 |
| WO | WO 2007/149032 | 12/2007 |
| WO | WO 2008/081008 | 7/2008 |
| WO | WO 2008/110372 | 9/2008 |
| WO | WO 2010/003529 | 1/2010 |

OTHER PUBLICATIONS

Fraussen et al. "A novel method for making human monoclonal antibodies" J of Autoimmunity 35, (2010) 130-134.*
Decker et al. "Immunostimulatory CpG-oligonucleotides induce functional high affinity IL-2 receptors on B-CLL cells: costimulation with IL-2 results in a highly immunogenic pheynotype" Experimental Hematology 28 (2000) 558-568.*
International Preliminary Report on Patentability and Written Opinion for International (PCT) Patent Application No. PCT/EP2013/050024 dated Jul. 10, 2014, 18 pages.
International Search Report for International (PCT) Patent Application No. PCT/EP2013/050026 dated May 7, 2013, 5 pages.
International Search Report for International (PCT) Patent Application No. PCT/EP2013/050024 dated Jun. 11, 2013, 8 pages.
Hu et al., "The IL-17 pathway as a major therapeutic target in autoimmune diseases," Annals of the New York Academy of Sciences, 2011, vol. 1217, pp. 60-76.
Jury et al., "Isolation and Functional Characterization of Recombinant GAD65 Autoantibodies Derived by IgG Repertoire Cloning From Patients With Type 1 Diabetes," Diabetes, 2001, vol. 50, Iss. 9, pp. 1976-1982.
Kisand et al., "Chronic mucocutaneous candidiasis in APECED or thymoma patients correlates with autoimmunity to Th17-associated cytokines," Journal of Experimental Medicine, 2010, vol. 207, No. 2, pp. 299-308.

(Continued)

*Primary Examiner* — Daniel E Kolker
*Assistant Examiner* — James Rogers
(74) *Attorney, Agent, or Firm* — Sheridan Ross P.C.

(57) ABSTRACT

Provided is a novel method of isolating and producing human antibodies with desired specificity from human B cells. In particular, a method of isolating human antibodies from memory B cells obtained from patients which suffer from a disease which is caused by or involves activation of the immune system, for example autoimmune and inflammatory disorders is described.

14 Claims, 5 Drawing Sheets

(56) References Cited

OTHER PUBLICATIONS

Kisand et al., "Interferon autoantibodies associated with AIRE deficiency decrease the expression of IFN-stimulated genes," Blood, 2008, vol. 112, No. 7, pp. 2657-2666.

Madec et al., "Four IgG Anti-Islet Human Monoclonal Antibodies Isolated from a Type 1 Diabetes Patient Recognize Distinct Epitopes of Glutamic Acid Decarboxylase 65 and Are Somatically Mutated," Journal of Immunology, 1996, vol. 156, No. 9, pp. 3541-3549.

Meager et al., "Anti-Interferon Autoantibodies in Autoimmune Polyendocrinopathy Syndrome Type 1," PLOS Medicine, 2006, vol. 3, Iss. 7, pp. 1152-1164.

Puel et al., "Autoantibodies against IL-17A, IL-17F, and IL-22 in patients with chronic mucocutaneous candidiasis and autoimmune polyendocrine syndrome type I," Journal of Experimental Medicine, 2010, vol. 207, No. 2, pp. 291-297.

Simpson et al., "Autoantibodies to Alzheimer and Normal Brain Structures from Virus-Transformed Lymphocytes," Journal of Neuroimmunology, 1986, vol. 13, No. 1, pp. 1-8.

Traggiai et al, "An efficient method to make human monoclonal antibodies from memory B cells: potent neutralization of SARS coronavirus," Nature Medicine, 2004, vol. 10, No. 8, pp. 871-875.

Tsuchiyama et al, "Synergy between anti-CD40 MAb and Epstein-Barr virus in activation and transformation of human B lymphocytes," Human Antibodies, 1997, vol. 8, No. 1, pp. 43-47.

MacCallum et al., "Antibody-antigen Interactions: Contact Analysis and Binding Site Topography," J. Mol. Biol., 1996, vol. 262, pp. 732-745.

Padlan et al., "Structure of an antibody-antigen complex: Crystal structure of the HyHEL-10 Fab-lysozyme complex," Proc. Natl. Acad. Sci. USA, 1989, vol. 86, pp. 5938-5942.

Restriction Requirement for U.S. Appl. No. 14/369,467, dated Jun. 24, 2015, 7 pages.

Official Action for U.S. Appl. No. 14/369,467, dated Sep. 8, 2015, 14 pages.

Final Action for U.S. Appl. No. 14/369,467, dated Mar. 1, 2016, 8 pages.

Notice of Allowance for U.S. Appl. No. 14/369,467, dated Jun. 30, 2016, 8 pages.

\* cited by examiner

METHOD OF ISOLATING HUMAN ANTIBODIES

CROSS-REFERENCE TO RELATED APPLICATIONS

This application is a national stage application under 35 U.S.C. 371 and claims the benefit of PCT Application No. PCT/EP2013/050026 having an international filing date of Jan. 2, 2013, which designated the United States, which PCT application claimed the benefit of U.S. Provisional Application No. 61/580,837 filed Dec. 28, 2011, and European Application No. 11195952.4 filed Dec. 28, 2011, the disclosures of each of which are incorporated herein by reference.

FIELD OF THE INVENTION

The present invention relates to a method of producing recombinant human antibodies with desired specificity derived from human B cells. In particular, the present invention provides a method of isolating human antibodies from memory B cells obtained from patients which suffer from a disease which is caused by or involves activation of the immune system, for example autoimmune and inflammatory disorders.

BACKGROUND OF THE INVENTION

Immunotherapy has raised great interest in the therapy of substantially every disease which can be targeted to an undesired antigen, for example a pathogen, tumor antigen, growth factors or pathologic protein aggregates. On the other hand, antibody responses in a subject may be the cause of a disease, for example in autoimmune and some inflammatory disorders, where autoantibodies for some reason attack endogenous proteins, cells and tissue.

In the past decades several technologies have been developed to isolate monoclonal antibodies and to produce humanized or fully human antibodies; see, e.g., references cited in international application WO 2007/068758 also granted as European patent EP 1 974 020 B1, in particular in sections [0002] to [0027], the disclosure content of which is incorporated herein by reference.

Typically, the isolation of antibodies, for example monoclonal antibodies, from B cells relies on cloning and expression of the immunoglobulin genes. This can be done by using phage display libraries of scramble $V_H$ and $V_L$ genes from B cells, or by isolation of paired $V_H$ and $V_L$ genes from single B cells using single cell PCR or from immortalized B cell clones.

Hitherto, the prior art was aiming at providing methods for establishing more optimized processes in which a high-through-put analysis of the secreted antibodies can be performed on the largest possible population of immortalized antibody-secreting cell lines maintained in cell culture conditions. In this context, several means and methods were investigated in order to enhance the efficiency of EBV immortalization and of cellular cloning of EBV-immortalized cells; see, e.g., international applications WO 2004/076677 and WO 2007/068758.

Almost all methods for obtaining immortalized antibody secreting cells have been established with B lymphocytes from healthy donors or infectious disease patients, which showed reactivity with viral antigens; see, e.g., Traggiai et al., Nat. Med. 10 (2004), 871-875 and Funaro et al., BMC Biotechnology 8 (2008), 85.

However, the current methods may not be as efficient for the isolation of antigen-independent memory B cells from patients experiencing an aberrant immune response, for example in autoimmune disorders wherein subsets of B and T lymphocytes become anergic, prone to apoptosis or otherwise dysregulated. For example, distinct mature B-cell subsets that accumulate with age, termed age-associated B cells have been discovered in mice, which are uniquely responsive to innate stimuli and refractory to CD40 and BCR stimulation; see, e.g., Hao et al., Blood 118 (2011), 1294-1304. They appear to be generated from mature B cells that exhaustively expand during the individual's lifetime and thus may represent an "exhausted" lymphocyte cell population. Moreover, an $IgD^- CD27^-$ population, possibly corresponding to exhausted memory B cells accumulates in elderly humans; see, e.g., Colonna-Romano et al., Mech. Ageing Dev. 130 (2009), 681-690. Furthermore, the immortalization efficiency of memory B cells from severely infected patients such as HIV-1 patients which typically also suffer from opportunistic diseases was reported to be significantly lower than that of non-HIV-1 infected donors. This finding was discussed to be due to the presence of "exhausted" memory B cells, characterized by the expression of inhibitory receptors and low levels of CD21; see, e.g., Moir et al., Nat. Rev. Immunol. 9 (2009), 235-245.

For the same reasons, phenotypically distinct populations of autoreactive B cells that have become functionally limited upon stimulation and/or display reduced viability in cell culture conditions may be found at increased frequency in autoimmune and some inflammatory diseases. It has been shown that self-Antigen (Ag) recognition results in severely diminished IgG response (Detanico et al., J. Immunol. 189 (2012), 4275-4283; Chumley et al., J. Immunol. 169 (2002), 1735-1743). Autoreactive B cells that can be found in patients with autoimmune and some inflammatory diseases are likely to be continually exposed to antigens and therefore anergic (Gauld et al, Nat. Immunol. 6 (2005), 1160-1167). These cells are expected to be functionally limited upon stimulation and/or display reduced viability in cell culture conditions.

Therefore, memory B cells from patients suffering from for example autoimmune or inflammatory diseases, in particular characterized by disregulated memory B cells or exhausted and less viable B cells, respectively, may not be sufficiently amenable to current immortalization protocols. However, such patients because of their immunoglobulin repertoire matured during the course of their disease may provide a valuable source of human antibodies against various therapeutic targets.

Accordingly, it would be highly desirable to provide methods for establishing processes in which, by applying specific means and conditions in cell culture for improving the viability and level of immunoglobulin production sufficient for the characterization of the immunoglobulin secreted B cells and cloning of corresponding immunoglobulin gene repertoire.

This problem has been solved by the embodiments characterized in the claims and following below as illustrated in the Examples and Figures.

SUMMARY OF THE INVENTION

The present invention is based on the observation that in order to arrive at B cells that secrete antibodies of specific isotypes in high amounts, from which the corresponding $V_H$ and $V_L$ genes can be cloned, cells need not to be immortalized but it is sufficient to provide them only the early polyclonal B cell activator function of Epstein-Bar virus (EBV). As illustrated in the Examples and shown in FIGS. 2 to 4 using this approach B cells were induced to secrete human antibodies of the IgG isotype thus allowing the detection and cloning of immunoglobulins and antibodies of interest, respectively, which are present within the memory B cells culture only in rare amounts or which for the reasons mentioned above would have been lost during the attempt of cellular cloning which requires long-term cultures and therefore immortalization of B cells.

Therefore, in a general aspect the present invention relates to a method of isolating and producing, respectively, a human antibody or binding fragment thereof with desired antigen specificity as illustrated in FIGS. 1 and 6, respectively, characterized by providing short term oligoclonal cultures of activated B cells, preferably memory B cells that secrete antibodies of the IgG isotype, wherein a B cell culture isolated from peripheral blood mononuclear cells (PBMCs) is subjected to a polyclonal B cell activator such as EBV under conditions which are sufficient for stimulating/activating proliferation and immunoglobulin secretion and without relying on the immortalizing properties of EBV.

Furthermore, since in contrast to the EBV based methods used in the prior art the B lymphocytes are not immortalized but only stimulated/activated with EBV the antibodies are isolated by molecular cloning, i.e. single cell harvest of oligoclonal cultures producing the antibody of interest and cloning the variable region of the immunoglobulin genes from single cells, rather than by cellular cloning, i.e. producing cell lines from immortalized B cells and "cloning" of oligoclonal cultures producing the antibody of interest by limiting dilution as taught for example in international applications WO 2004/076677 and WO 2007/068758.

As illustrated in FIGS. 1 and 6, a primary screen with B cell culture supernatants tested at a single dilution on the antigen of interest can be performed using, e.g., ELISA screening. Confirmatory screen with B cell culture supernatant tested at different dilutions on the antigen of interest and control antigens may be performed as well. Cultures reactive with the antigen of interest, but not with other antigens are single cell sorted.

Antibody isolation is performed by molecular cloning. Immunoglobulin genes of single cell sorted cells are sequenced and cloned into expression vectors. Recombinant antibodies are expressed in HEK293 T cells and supernatants containing the recombinant antibodies tested for their specific binding to the target of interest.

1. Cells are plated immediately after sort in RPMI medium without Tf supplemented with 20% EBV supernatant of B95-8 cells and 2.5 ug/ml CpG, with 50,000 feeders/well.

2. Cells are incubated for 4 h 30' with EBV (50% supernatant of B95-8 cells), diluted 1:230 (0.2% EBV supernatant) in IMDM medium supplemented with Tf and 2.5 ug/ml CpG and plated with 30,000 feeders/well.

3. Cells are incubated for 4 h 30' with EBV (50% supernatant of B95-8 cells), diluted 1:230 (0.2% EBV supernatant) and centrifuged to eliminate supernatant, then resuspended and plated in IMDM medium supplemented with Tf and 2.5 ug/ml CpG (<0.0002% EBV supernatant) and plated with 30,000 feeders/well.

4. As #3, but with different feeders.

5. As #4, but in IMDM medium without Tf supplemented with 2.5 ug/ml CpG.

6. Cells are incubated for 3 h 30' with EBV (50% supernatant of B95-8 cells), diluted 1:230 (0.2% EBV supernatant) in RPMI medium without Tf supplemented with 2.5 ug/ml CpG and plated with 50,000 feeders/well.

7. Cells are incubated for 3 h 30' with EBV (50% supernatant of B95-8 cells), diluted 1:230 (0.2% EBV supernatant) in IMDM medium without Tf supplemented with 2.5 ug/ml CpG and plated with 30,000 feeders/well.

8. As #7, but in IMDM medium supplemented with Tf and 2.5 ug/ml CpG.

9. As #8, but with 50,000 feeders/well.

Figure 1:
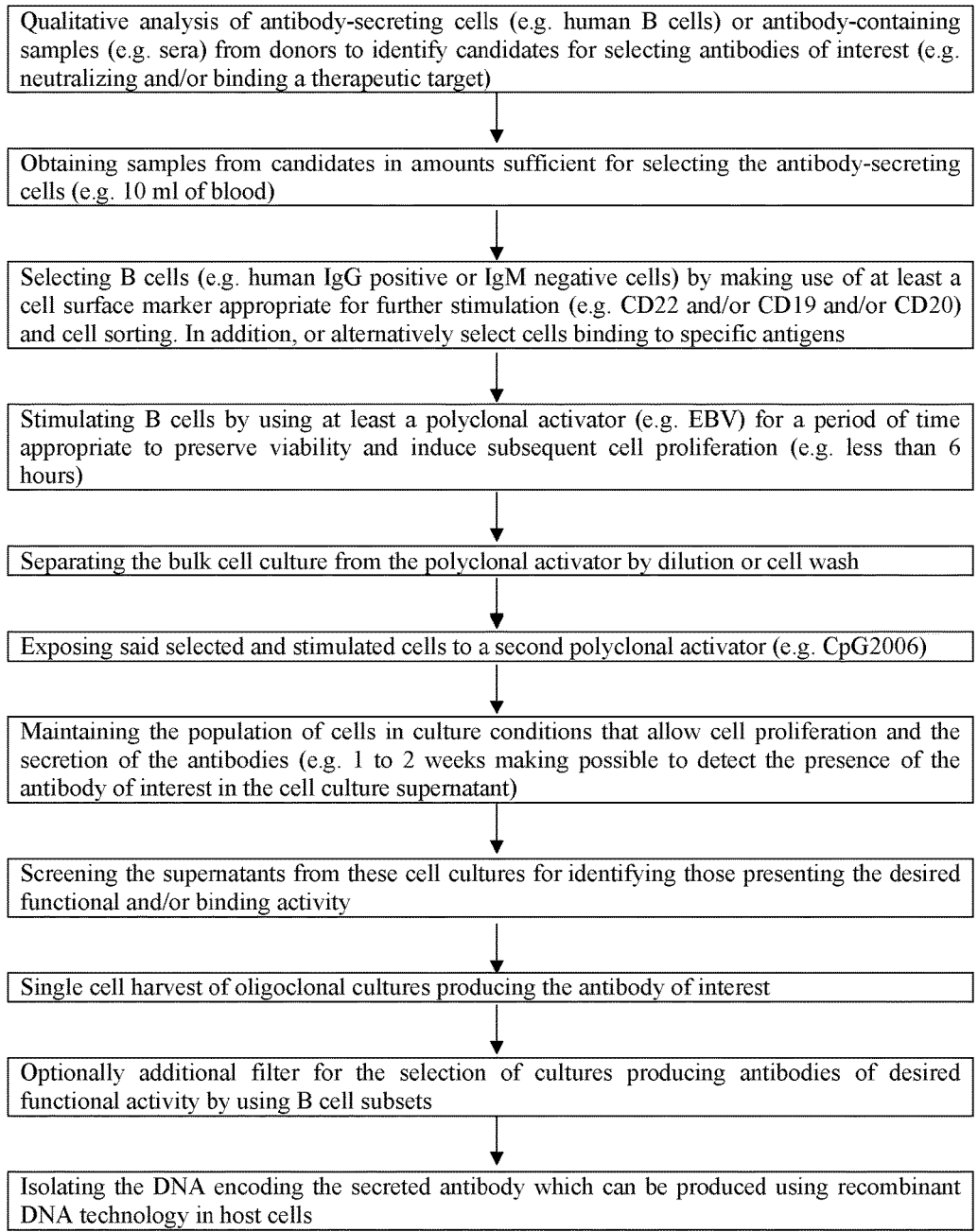
FIG. 1: Schematic representation of a process for isolating and expressing monoclonal antibodies including the method of the present invention for obtaining short term oligoclonal cultures of activated B cells. First donors are analyzed for B cell or serum reactivity (includes specific antigens of interest, protoarrays or expression libraries). Then B cells are isolated, stimulated and maintained in short-term cultures to allow proliferation and secretion of antibodies in the supernatant that can be screened. Positive cultures producing the antibody with the desired function and/or binding activity are single cells harvested. Finally, antibodies are isolated by molecular cloning of immunoglobulin genes from single cell sorted cells.
Figure 3:
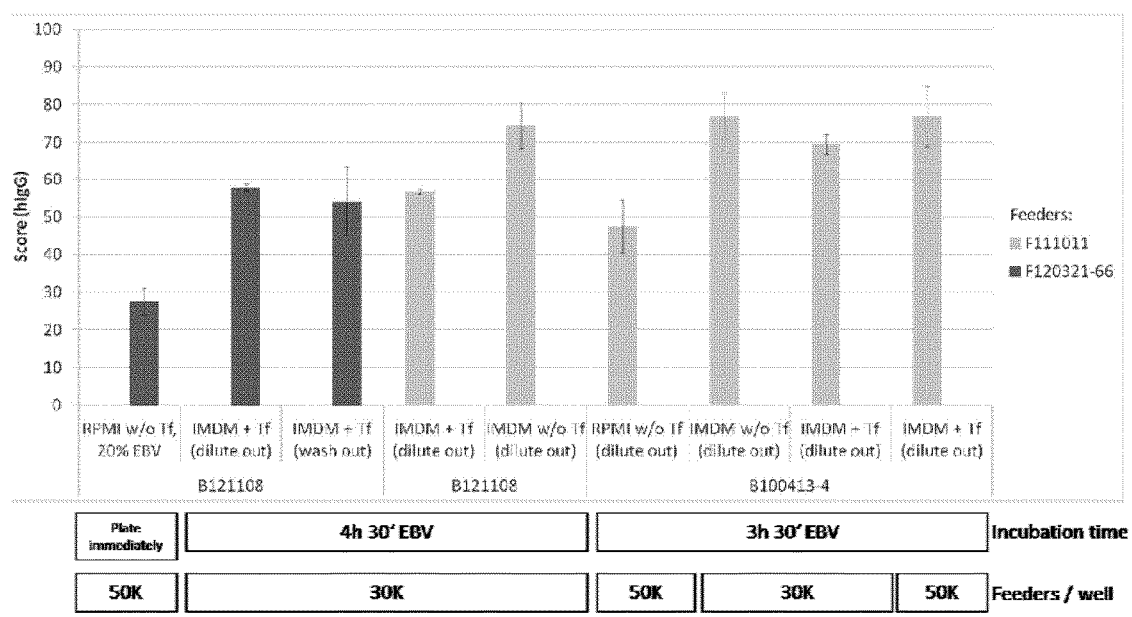
FIG. 3: Ig production of memory B cells activated with EBV and CpG according to different procedures. First, it was tried to improve protocols using EBV and CpG by incubating cells with EBV for a limited time and then either diluting it out by plating cells in medium containing CpG but not EBV (dilute out), or eliminating EBV through cell wash before plating in medium with containing CpG but not EBV (wash out). Further, IgG production by cells plated in different media (RPMI 1640 or IMDM) in the presence or absence of transferrin (Tf) was investigated since transferrin was reported to support growth of B lymphoblasts immortalized with EBV (Gordon, J. Exp. Med. 159 (1984), 1554-1559). Memory B cells were sorted from frozen PBMC samples from healthy donors, exemplary shown for B100413-4 and B121108) cultured at 10 cells/well in 96-well U-bottom plates in different media with different % of EBV. After 10-11 days culture supernatants from two plates per condition were diluted 1:9 and tested by ELISA for the presence of human IgG (hIgG). Reported is the percentage of wells with hIgG levels above the average between the three highest and three lowest cultures (average of results of two plates). Bars.
Figure 4:
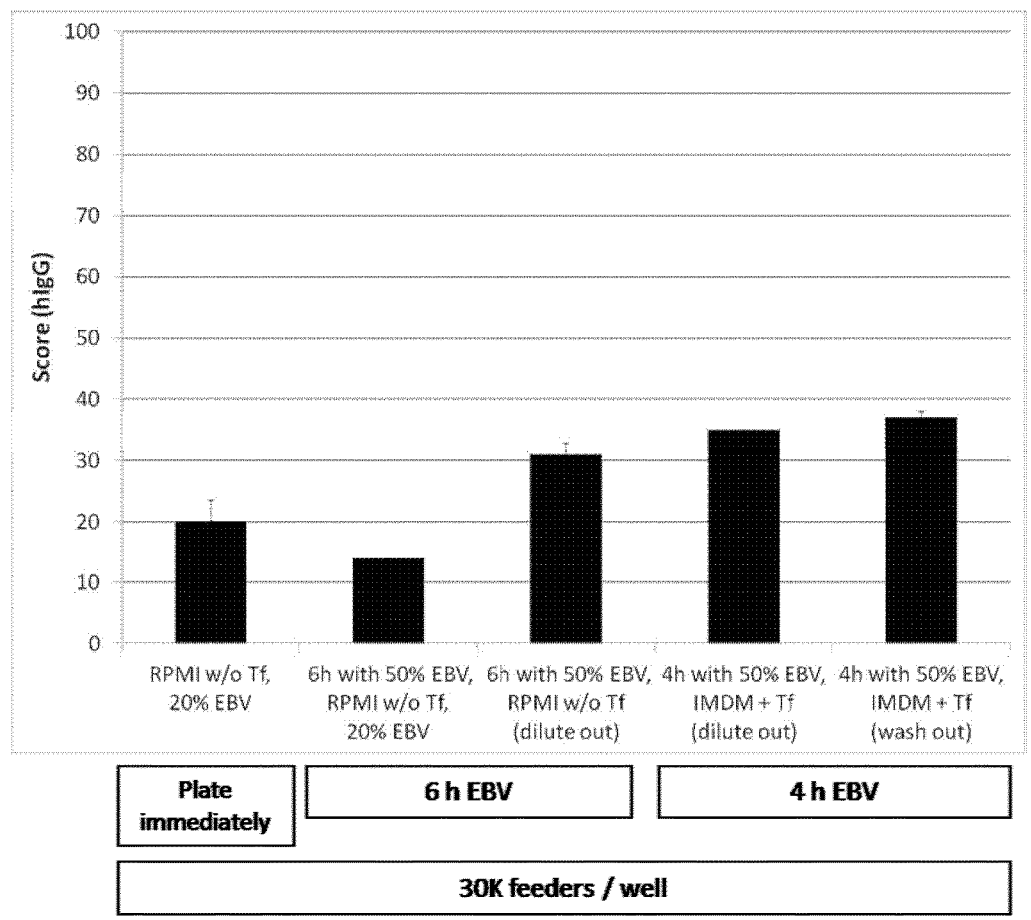

FIG. 4: Exemplary results of experiments aiming at comparing the extent of Ig production of B memory cells prepared according to the method of B cell immortalization as described in Traggiai et al. Nat. Med. 2004; see supra, and EP 1 597 280 B1, i.e. plating cells in medium with EBV (20% based on Example 8 of EP 1 597 280 B1)+CpG (#1), or 6 h with 50% EBV before plating in medium with EBV+CpG (based on Example 3 of EP 1 597 280 B1) (#2) and the method of the present invention as illustrated in FIG. 1, i.e. providing a short term oligoclonal cultures of B memory cells activated by incubation with EBV for a limited time (4-6 hours) and then stimulated with CpG (#3 to 5). In all cases 30,000 feeder cells/well were used. After 11 days culture supernatants are tested as in FIG. 3. Bars:

1. Cells are plated immediately after sort in RPMI medium without Tf supplemented with 20% EBV supernatant of B95-8 cells and 2.5 ug/ml CpG.

2. Cells are incubated for 6 h with EBV (50% supernatant of B95-8 cells) and plated in RPMI medium without Tf supplemented with 20% EBV supernatant of B95-8 cells and 2.5 ug/ml CpG.

3. Cells are incubated for 6 h with EBV (50% supernatant of B95-8 cells), diluted 1:230 (0.2% EBV supernatant) in RPMI medium without Tf supplemented with 2.5 ug/ml CpG.

4. Cells are incubated for 4 h with EBV (50% supernatant of B95-8 cells), diluted 1:230 (0.2% EBV supernatant) in IMDM medium supplemented with Tf and 2.5 ug/ml CpG.

5 Cells are incubated for 4 h with EBV (50% supernatant of B95-8 cells), diluted 1:230 (0.2% EBV supernatant) and centrifuged to eliminate supernatant, then resuspended and plated in IMDM medium supplemented with Tf and 2.5 ug/ml CpG (<0.0002% EBV supernatant).

Figure 5:
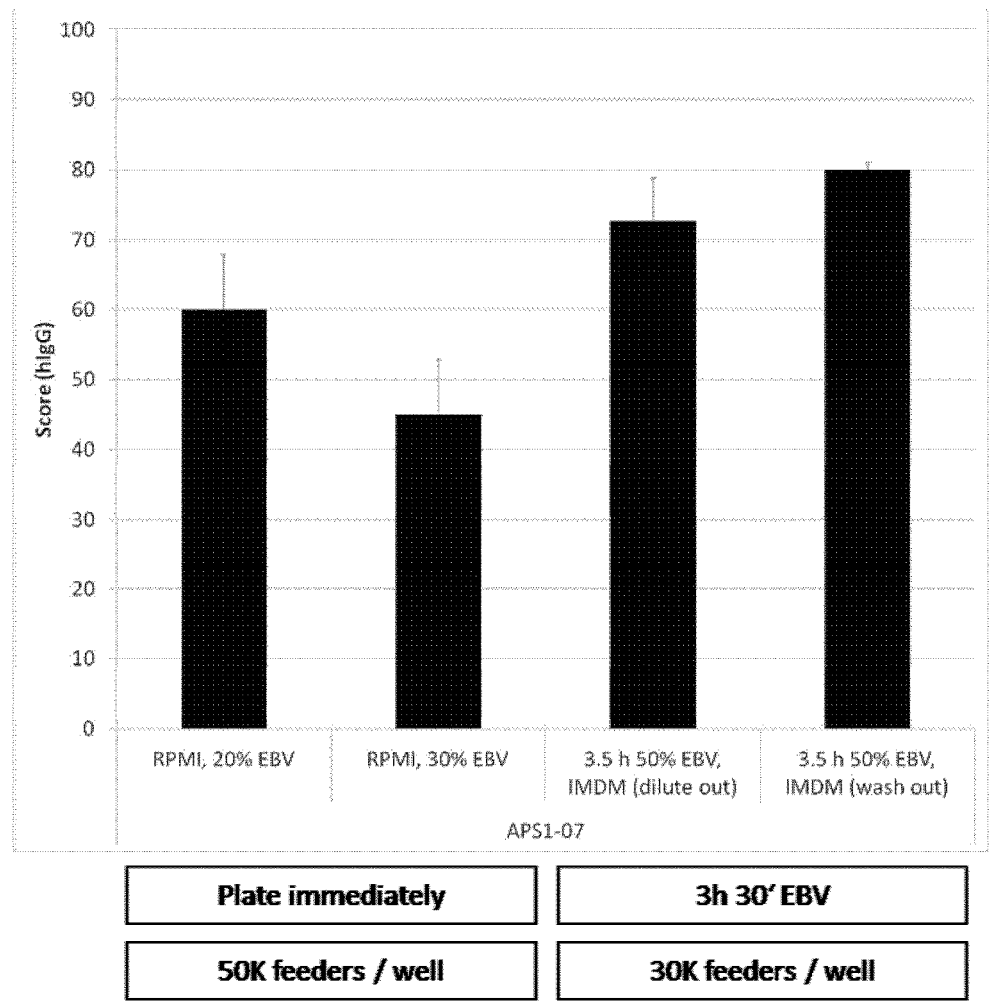

FIG. 5: Ig production of EBV activated memory B cells derived from APS1 patients. Memory B cells were sorted from frozen PBMC from APS1-07 patient and cultured at 10 cells/well in media with 20% EBV (as taught in EP 1 597 280 B1, Example 8) (#1), or 30% of EBV (as taught in Traggiai et al., see supra) (#2) supplemented with 2.5 ug/ml CpG, and the method of the present invention as illustrated in FIG. 1, i.e. providing a short term oligoclonal cultures of B memory cells activated by incubation with EBV for a limited time (3.5 hours) and diluting or washing out EBV (#4 and 5, respectively) before providing the second polyclonal stimulator CpG. After 10 days culture supernatants were tested as in FIG. 3. Bars:

1. Cells are plated immediately after sort in RPMI medium supplemented with 20% EBV supernatant of B95-8 cells and 2.5 ug/ml CpG with 50,000 feeders/well.

2. Cells are plated immediately after sort in RPMI medium supplemented with 30% EBV supernatant of B95-8 cells and 2.5 ug/ml CpG with 50,000 feeders/well.

3. Cells are incubated for 3 hours 30 minutes with EBV (50% supernatant of B95-8 cells), diluted 1:230 (0.2% EBV supernatant) in IMDM medium supplemented with 2.5 ug/ml CpG with 30,000 feeders/well.

4. Cells are incubated for 3 hours 30 minutes with EBV (50% supernatant of B95-8 cells), diluted 1:230 (0.2% EBV supernatant) and centrifuged to eliminate supernatant, then resuspended and plated in IMDM medium supplemented with 2.5 ug/ml CpG (<0.0002% EBV supernatant) and plated with 30,000 feeders/well.

Figure 6:
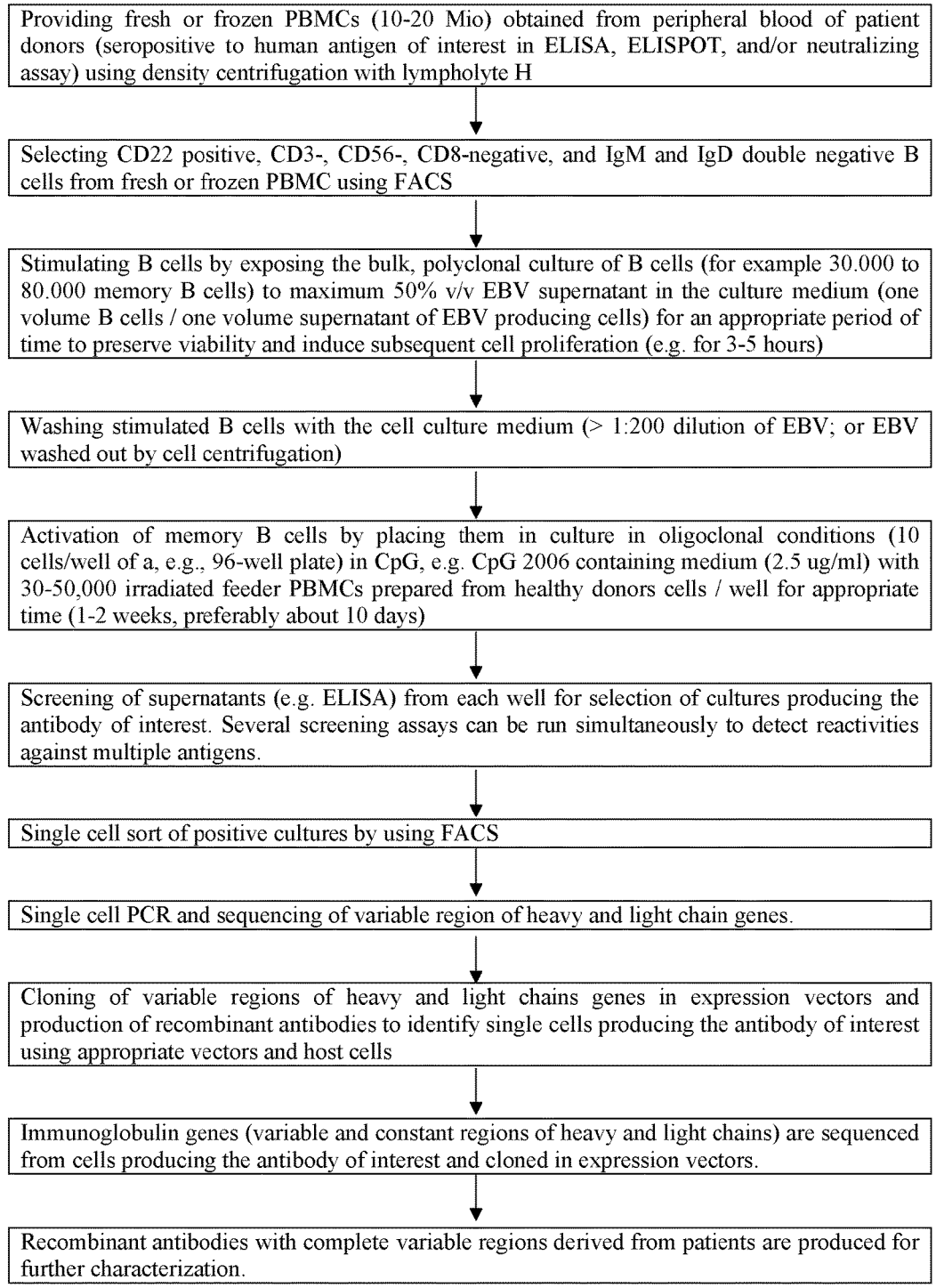

FIG. 6: Schematic representation of a general preferred process for identifying human B cells secreting IgG antibodies that bind and/or neutralize human antigens comprising the methods of the present invention for providing short term oligoclonal cultures of antibody-secreting cells; such as human memory B cells.

DISCLOSURE OF THE INVENTION

As mentioned hereinbefore, the present invention generally relates to a method of producing a human antibody or binding fragment thereof with desired antigen specificity as illustrated in FIGS. 1 and 6, respectively, characterized by providing short term oligoclonal cultures of activated B cells, preferably memory B cells that secrete antibodies of the IgG isotype, wherein a B cell culture isolated from peripheral blood mononuclear cells (PBMCs) is subjected to a polyclonal B cell activator such as EBV under conditions which are sufficient for stimulating/activating proliferation and immunoglobulin secretion and without relying on the immortalizing properties of EBV; and isolating the antibody of interest by molecular cloning, i.e. single cell harvest of oligoclonal cultures producing the antibody of interest and cloning the variable region of the immunoglobulin genes from single cells.

As indicated in the Examples and illustrated in FIGS. 1 and 6, the memory B cells were first stimulated with a first polyclonal B cell activator, i.e. by incubation with EBV containing supernatant obtained from B95-8 cells for a limited time and then separated by seeding in a different medium with a second polyclonal B cell activator, i.e. CpG2006.

In fact, during experiments performed within the scope of the present invention it turned out that previous methods aiming at B cell immortalization for providing a B cell clone producing the antibody of interest such as those described in international application WO 2004/076677 do not work quite well if at all for B cells of patients suffering from APECED/APS1 displaying an auto-immunosome, i.e an autoantibody profile which in its variety is outstanding and represents a broad spectrum of binding molecules specific for proteins prone to invoke an autoimmune response and/or potentially associated to disorders related to an undesired autoimmune response or other autoimmune diseases. APS1 is a rare autoimmune disease caused by mutations in the Autoimmune Regulator (AIRE) gene. The AIRE protein governs the expression in medullary thymic epithelium of many peripheral self-antigens (e.g., insulin) that are presented by MHC to tolerise developing thymocytes. In APS-1, AIRE mutations cause aberrant negative selection, which enables autoreactive T cells to escape to the periphery; see, e.g., Kisand et al., Eur. J. Immunol. 41 (2011), 1517-1527; Peterson et al., Nat. Rev. Immunol. 8 (2008), 948-957 and Kluger, Ranki and Krohn Front. Immunol. 3 (2012), 232 for review. In this context, and in view of the results obtained in the experiments performed in accordance with the present invention the loss or a defect of regulatory T cells in patients suffering from autoimmune disorders, in particular observed in APECED patients (see, e.g., Laakso et al., J. Autoimmun. 35 (2010), 351-357; Kekäläinen et al., J. Immunol. 178 (2007), 1208-1215) may be the cause for the above-mentioned auto-immunosome.

Without intending to be bound by theory, it is believed that due to the impaired tolerance or loss of self-tolerance of the immune system, B cells, in particular those which are of interest in accordance with the present invention, have been pre-activated or triggered through a signaling pathway otherwise which induces or is associated with the induction of apoptosis for which reason those cells have only a limited life span and are no longer effectively amenable to immortalization perhaps similar to "exhausted" memory B cells reported in the prior art, at least not under the conditions hitherto reported for EBV-mediated immortalization. In view of the findings made in experiments performed in accordance with the present invention but without intending to be bound by theory it is believed that the simultaneous occurrence of cytokine and anti-cytokine antibodies such as observed in APECED/APS1 patients will lead to immune complex formation which could bind to B cells and activate them, thus explaining an activated state of B cells from APS1 patients and their vulnerability to senescence.

However, as illustrated in the Examples and mentioned above, in accordance with the present invention a method is provided to isolate the human antibodies by treating and culturing the memory B cells under short term oligoclonal culture conditions allowing only a definite life span of the B cells during activation with subsequent single cell or bulk harvesting of oligoclonal cultures producing the antibody of interest and cloning the cDNA of the variable region of the antibody.

Accordingly, in one embodiment the present invention relates to a method of producing a human antibody or binding fragment thereof with desired antigen specificity characterized by isolating B cells from short term oligoclonal cultures of activated B cells that secrete antibodies of IgG isotype comprising the following steps in the sequence:
(a) selecting B cells that express antibodies against a protein of interest from one or more biological samples;
(b) stimulating the selected cells with a first polyclonal B cell activator under cell culture conditions;
(c) separating the cells from said activator;
(d) activating the stimulated cells with a second polyclonal B cell activator under cell culture conditions;
(e) screening the activated cells that express IgG isotype antibodies of interest and preferably;
(e') single-cell harvesting of oligoclonal cultures producing the antibody of interest;
(f) sequencing and/or cloning the cDNA of at least the variable light and heavy chain regions and optionally constant region of the antibody of interest.

The term "oligoclonal culture" refers to a culture of cells producing the antibody of interest derived from one or a few cells that have been activated. Preferably, the oligoclonal culture is derived from one single B cell, which may also be referred to as "B cell clone". As mentioned above, and unless stated otherwise, the terms "oligoclonal" and "clone" do not imply or refer to immortalized cells. As illustrated in the Examples, the biological sample is preferably derived from peripheral blood mononuclear cells of a patient whose serum has been screened for the presence of auto-antibodies against the protein of interest.

Typically, the B cells that express antibodies against a protein of interest are selected on the basis of the expression of at least one B cell-surface membrane marker such as preferably CD22. However, in addition or alternatively the B cells are selected on the basis of their binding to the antigen using for example ELISPOT.

Preferably, the B cells are memory B cells, in particular human memory B cells and are depleted from IgM and/or IgD isotypes already before exposure to the first polyclonal activator, for example by FACS using appropriate B cell-surface membrane marker specific antibodies; see also the Examples.

The antibody-producing cells are isolated, stimulated, and proliferated according to the methods of the present invention in bulk cultures for a variable number of hours (e.g. from 1 up to 6 hours, or less preferred for longer periods of time such as 6 to 12 hours) before being subdivided into several pools of about 10 cells per culture for stimulation by the second polyclonal activator, each representing a population of cells, that are cultured separately (e.g. 96-, 384- or 1536 well plates). The bulk, polyclonal population of cells maintained in cell culture conditions may be tested using the assays performed already on sera to select the donor, or any other assay relevant for future use of the cells, in order to confirm the presence of cells. Moreover, some aliquots of the polyclonal population of cells may be put in vials and stored as frozen cells (as normally done for established mammalian cell lines), to be thawed and cultured again later. In this context, it is intended that the same culture supernatant can be tested on several different antigens, possibly all the antigens against which serum reactivity of the biological samples have been determined, e.g., in a protoarray.

Aliquots of the cell culture supernatant can be screened for their binding and/or functional activity in a high through-put manner, in order to identify the positive well(s) presenting the desired activity, possibly using a dose-response analysis with serially diluted culture supernatants or partially purified antibody preparations (e.g. obtained by affinity chromatography on protein A columns) in parallel experiments. Optionally, the positive pools of cells (i.e. those showing the desired antigen specificity and/or biological activity) can be then used to generate a new series of pools of cells to further restrict the screening to the level of a single cell culture(s) and consequently isolate the cDNA of the antibody variable regions form the selected cell secreting a monoclonal antibody having the desired specificity and activity, at least at the level of the initial screening assay. The selected monoclonal antibodies should be then re-evaluated using other more demanding functional assays and characterized at the level of isotype and of $V_H/V_L$ sequence, after isolating them using the recombinant DNA technologies applicable on B cells.

As further illustrated in the Examples, the first polyclonal B cell activator is preferably Epstein-Barr virus (EBV) and/or the second polyclonal B cell activator is preferably a CpG-based oligonucleotide.

Though EBV and CpG, in particular CpG2006 (ODN 2006 according to Hartmann et al., J. Immunol. 164 (2000), 1617-1624) are used as the preferred first and second polyclonal B cell activator, respectively, other polyclonal B cell activators are known to the person skilled in the art; see, e.g., European patent EP 1 974 020 B1, in particular for the first polyclonal B cell activator in accordance with the present invention at page 13, paragraph [0115] to page 14, paragraph [0126], the disclosure content of which is incorporated herein by reference and for the second polyclonal B cell activator such as TLR agonists with similar properties as CpG at page 12, paragraph [0096] to page 13, paragraph [0104], in particular CpG2006 illustrated by SEQ ID NO: 1 in paragraph [0177], and European patent EP 1 597 280 B1 at page 5, paragraphs [0014] to [0022], the disclosure content of which is incorporated herein by reference.

In this context, it is noted that though EBV has been used in the prior art for immortalizing B cells, EBV and like viral immortalizing agents have dual activities, i.e. besides the capability of immortalizing B cells under appropriate cell culture conditions to also independently activate the B cells inducing both proliferation and Ig secretion. This early function of EBV is distinct from its late function of immortalizing B cell lines as shown by Tsuchiyama et al., Hum. Antibodies 8 (1997), 43-47. Accordingly, the present invention only makes use of the early function as a polyclonal B cell activator of EBV and of similar viral immortalizing agents but not of the late function as a transforming virus capable of generating immortalized B cell lines that can be maintained in cell culture for several months, thereby only providing and using short term oligoclonal cultures of activated B cells with limited life span as further described below. Making use of only the early function of EBV and like agents can be accomplished by adjusting the time of culturing the cells in the presence of EBV only to the extent necessary to achieve a stimulation of the cells, i.e. proliferation of the cells and antibody secretion, with subsequent separation of the cells from EBV and like agents or vice versa.

As further turned out in the experiments performed within the scope of the present invention and illustrated in the Examples, the presence of a cytokine such as interleukin-2 (IL-2) as taught in European patent EP 1 974 020 B1 and EP 1 597 280 B1 or other costimulatory molecules such transferrin is not necessary. Rather, it turned out that in the method of the present invention the presence of cytokines in the B cell culture have substantially no beneficial effects, probably because of the mentioned preactivation or signaling in the B cells. Accordingly, in a preferred embodiment of the method of the present invention the culture conditions in step (b) and/or step (d) do not comprise a cytokine.

Typically, the stimulation of the selected cells with the first polyclonal B cell activator lasts less than 8 hours, preferably less than 6 hours and in the particular preferred embodiment of the method of the present invention the selected cells in step (b) are stimulated for about three to five hours.

After activation, the B cells are separated from the first polyclonal B cell activator in step (c), wherein the activator is removed for example by diluting off or washing out. In this context, experiments performed in accordance with the present invention confirmed that the presence of the first polyclonal B cell activator is indeed no longer necessary by ensuring the total removal of any thereof using multiple washing steps before subjecting the stimulated cells to the second polyclonal B cell activator. Nevertheless, for the purposes of the method of the present invention it is usually efficient to remove the first polyclonal B cell activator by diluting off, i.e. seeding the B cells in fresh culture medium. Thus, the cell culture subjected to the first polyclonal B cell activator may be placed in fresh culture media containing the second polyclonal activator thereby diluting the medium with the first polyclonal activator to a maximum of about 10%, preferably 5%, more preferably to 1%, and most preferably substantially below 1%, for example 0.5%, 0.1% or less.

Typically, during the culture in the presence of the second polyclonal activator the B cells are seeded at low concentration of cells per culture, for example in wells of microtiter culture plate. Preferably, the concentration of cells per well is 5 to 20, more preferably 5 to 15 and most preferably 10.

As mentioned hereinbefore and illustrated in the Examples, in step (d) the stimulated B cells are cultured in the presence of the second polyclonal B cell activator such as CpG no more than one to two weeks until singling out the cells from the B cell cultures which are reactive against the desired antigen. In a preferred embodiment of the method of the present invention, the transferred selected cells are exposed in step (d) to the second polyclonal activator for about eight to fourteen days. Preferably, in step (d) and/or (e) the cells are cultured under oligoclonal conditions with about ten cells per well in eight to fourteen days short term cultures.

The methods of the invention can be applied for the identification of monoclonal antibodies expressed by human B cells selected from any suitable donors, i.e. can be naive, vaccinated, affected by one or more diseases or infections, already exposed and/or resistant to specific therapeutic treatments, presenting a specific clinical index or status, inadvertently exposed to a pathogen, etc. However, the method of the present invention seems to be particularly advantageous for the isolation of human antibodies from subjects suffering from an autoimmune disorder or inflammatory disease and similar diseases especially when accompanied by reduced viability and/or responsiveness of B memory cells.

Donor's sera can be used as such for an initial determination of their seropositivity to an antigen, since the specificity and long-term maintenance of the adaptive immune responses (even years after the last exposure to this antigen) may allow a qualitative determination that is sufficient for selecting donors. The nature and sensitivity of the screening assay used is critical in identifying the most suitable donor and, preferably, the assay used to screen donor serum should be the same as that used to screen supernatants from oligoclonal cultures of antibody-secreting B cells and designed to detect an antibody with the desired functional activity (i.e. neutralization and/or binding to the antigen of interest)

In the clinical context, the choice of the tissue or the organ from which the cells are purified can be dictated from the availability of the cells in sufficient amount for performing the whole process. Given that cells may be obtained from human clinical samples in small quantities and/or prepared in locations different from where the methods of the present invention may be performed, the cells can be obtained from frozen samples and/or from samples obtained from a number of individuals that have been pooled to provide enough starting material.

Thus, a preliminary screen can be done on a panel of candidate donors, using samples containing antibody secreting cells (such as total peripheral blood or serum). In particular, mononuclear cells can be isolated from blood or lymphatic tissues using standard separation techniques for isolating peripheral blood mononuclear cells (PBMCs), such as gradient centrifugation. After and/or before this separation step, the samples of sera (or plasma), cell culture supernatants, or cells (obtained from different patients, from different tissues, and/or at different time points) can be prescreened using standard technologies for detecting the presence of antibodies and antibody-secreting cells (e.g. ELISA, BIACORE, Western blot, FACS, SERPA, antigen arrays, neutralization of viral infection in a cell culture system, or ELISPOT assays). The literature provides several Examples of these technologies showing, for example, the use of ELISPOT for characterizing the immune response in vaccinated donors (Crotty et al., Immunol Meth. 286 (2004), 111-122), the use of antigen microarrays as diagnostic tools for newly infected patients (Mezzasoma et al., Clin Chem. 48 (2002), 121-130, and other technologies for measuring antigenspecific immune responses (Kern et al., Trends Immunol. 26 (2005), 477-484).

As mentioned, the method of the present invention is preferably employed using a biological sample derived from a subject suffering from an autoimmune disorder and/or inflammatory disease. As used herein, an "autoimmune disorder" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease that can affect multiple organ systems (for example, systemic lupus erythematosus (SLE), rheumatoid arthritis, polymyositis, autoimmune polyendocrinopathy syndrome type 1 (APS-1)/autoimmune polyendocrinopathy-candidiasis-ectodermal dystrophy (APECED) etc. Preferred such diseases include autoimmune rheumatologic disorders (such as, for example, rheumatoid arthritis, Sjogren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis (MS), opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, atopic dermatitis, urticaria, pemphigus group diseases, bullous pemphigoid diseases, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, autoimmune thyroid disease (e.g., Graves' disease and thyroiditis)) and diseases affecting the generation of autoimmunity such as autoimmune polyendocrinopathy syndrome type 1 (APS-1)/autoimmune polyendocrinopathy-candidiasis-ectodermal dystrophy (APECED) Myasthenia Gravis (MG/Thymoma. Preferred diseases include, for example, RA, IBD, including Crohn's disease and ulcerative colitis, ANCA-associated vasculitis, lupus, MS, Sjogren's syndrome, Graves' disease, IDDM, pernicious anemia, thyroiditis, and glomerulonephritis, and APS-1. Still more preferred are RA, IBD, lupus, and MS, and more preferred RA and IBD, and most preferred RA.

Specific examples of other autoimmune disorders as defined herein, which in some cases encompass those listed above, include, but are not limited to, arthritis (acute and chronic, rheumatoid arthritis including juvenile-onset rheumatoid arthritis and stages such as rheumatoid synovitis, gout or gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, osteoarthritis, arthritis chronica progrediente, arthritis deformans, polyarthritis chronica primaria, reactive arthritis, menopausal arthritis, estrogen-depletion arthritis, and ankylo sing spondylitis/rheumatoid spondylitis), autoimmune lymphoproliferative disease, inflammatory hyperproliferative skin diseases, psoriasis such as plaque psoriasis, gutatte psoriasis, pustular psoriasis, and psoriasis of the nails, atopy including atopic diseases such as hay fever and Job's syndrome, atopic dermatitis, allergic and toxic contact dermatitis (acute and chronic), exfoliative dermatitis, allergic dermatitis, hives, dermatitis herpetiformis, nummular dermatitis, seborrheic dermatitis, non-specific dermatitis, x-linked hyper IgM syndrome, allergic intraocular inflammatory diseases, urticaria such as chronic allergic urticaria and chronic idiopathic urticaria, cold urticarial, including chronic autoimmune urticaria, myositis, polymyositis/dermatomyositis, juvenile dermatomyositis, toxic epidermal necrolysis, scleroderma (including local and systemic forms of scleroderma), multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, gastrointestinal inflammation, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, graft-versus-host disease, angioedema such as hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, various forms of asthma, Chronic Obstructive Pulmonary Disease (COPD), encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN (RPGN), proliferative nephritis, autoimmune polyglandular endocrine failure, balanitis including balanitis circumscripta plasmacellularis, balano-posthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, epidermolytic hyperkeratosis, premalignant keratosis, pyoderma gangrenosum, allergic conditions and responses, food allergies, drug allergies, insect allergies, rare allergic disorders such as mastocytosis, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-0 blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus discoid lupus erythematosus including all its clinical forms, SLE, such as cutaneous SLE or subacute cutaneous SLE, neonatal lupus syndrome (NLE), and lupus erythematosus disseminatus, juvenile onset (Type I) diabetes mellitus, including pediatric IDDM, adult onset diabetes mellitus (Type II diabetes), autoimmune diabetes, idiopathic diabetes insipidus, diabetic retinopathy, diabetic nephropathy, diabetic colitis, diabetic large-artery disorder, immune responses associated with acute and delayed hypersensitivity mediated by cytokines and T-lymphocytes, tuberculosis, sarcoidosis, granulomatosis including lymphomatoid granulomatosis, agranulocytosis, vasculitides (including large-vessel vasculitis such as polymyalgia rheumatica and giant-cell (Takayasu's) arteritis, medium-vessel vasculitis such as Kawasaki's disease and polyarteritis nodosa/periarteritis nodosa, immuno vasculitis, CNS vasculitis, cutaneous vasculitis, hypersensitivity vasculitis, necrotizing vasculitis such as fibrinoid necrotizing vasculitis and systemic necrotizing vasculitis, A CA-negative vasculitis, and ANCA-associated vasculitis such as Churg-Strauss syndrome (CSS), Wegener's granulomatosis, and microscopic polyangiitis), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia(s), cytopenias such as pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, motoneuritis, allergic neuritis, Beliefs disease/syndrome, Castleman's syndrome, Goodpasture's syndrome, Reynaud's syndrome, Sjogren's syndrome, Stevens-Johnson syndrome, pemphigoid or pemphigus such as pemphigoid bullous, cicatricial (mucous membrane) pemphigoid, skin pemphigoid, pemphigus vulgaris, paraneoplastic pemphigus, pemphigus foliaceus, pemphigus mucus-membrane pemphigoid, and pemphigus erythematosus, epidermolysis bullosa acquisita, ocular inflammation, preferably allergic ocular inflammation such as allergic conjunctivis, linear IgA bullous disease, autoimmune-induced conjunctival inflammation, autoimmune polyendocrinopathies, Reiter's disease or syndrome, thermal injury due to an autoimmune condition, preeclampsia, an immune complex disorder such as immune complex nephritis, antibody-mediated nephritis, neuroinfammatory disorders, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia including, for example, idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, Grave's eye disease (ophthalmopathy or thyroid-associated ophthalmopathy), polyglandular syndromes such as autoimmune polyglandular syndromes, for example, type I (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, pneumonitis such as lymphoid interstitial pneumonitis (LIP), bronchiolitis obliterans (non-transplant) vs. NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia such as mixed cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, keratitis such as Cogan's syndrome/nonsyphilitic interstitial keratitis, Bell's palsy, Sweet's disease/syndrome, rosacea autoimmune, zoster-associated pain, amyloidosis, a noncancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia areata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, fibrosing mediastinitis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis (systemic inflammatory response syndrome (SIRS)), endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, conjunctivitis, such as vernal catarrh, keratoconjunctivitis sicca, and epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders (cerebral vascular insufficiency) such as arteriosclerotic encephalopathy and arteriosclerotic retinopathy, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica (sympathetic ophthalmitis), neonatal ophthalmitis, optic neuritis, orchitis granulomatosa, pancreatitis, polyradiculitis acuta, pyoderma gangrenosum, Quervain's thyreoiditis, acquired spenic atrophy, non-malignant thymoma, lymphofollicular thymitis, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, autoimmune polyendocrinopathies, oophoritis, primary myxedema, autoimmune atrophic gastritis, rheumatic diseases, mixed connective tissue disease, nephrotic syndrome, insulitis, polyendocrine failure, autoimmune polyglandular syndromes, including polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, allergic sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, spondyloarthropathies, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism such as chronic arthrorheumatism, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis.

As illustrated in FIGS. 1 and 6, cDNA will be prepared from single B cells sorted from the short term oligoclonal cultures of activated B cells secreting the antibody of interest in order to isolate and produce the monoclonal antibody of the present invention. Accordingly, the method of the present invention typically comprises the steps of:

(i) obtaining mRNA from bulk or single B cells sorted from short term oligoclonal cultures of activated B cells secreting the antibody of the invention;

(ii) obtaining cDNA from the mRNA of step (i);

(iii) using a primer extension reaction to amplify from said cDNA the gene repertoire corresponding to the heavy chains (HC) and the light chains (LC) and optionally constant domain of said antibodies;

(iv) using said repertoire to express said antibody or an antigen-binding fragment thereof in a host cell;

(v) identifying the antibody clone presumably responsible for the reactivity of the parental B cell culture; and (vi) isolating the monoclonal antibody or an antigen-binding fragment thereof;

optionally wherein the DNA is manipulated between steps (iii) and (iv) to introduce restriction sites, to change codon usage, introduce coding sequences for functional domains or peptide linkers; and/or to add or optimize transcription and/or translation regulatory sequences. RT-PCR of single sorted cells is preferably employed for obtaining the immunoglobulin gene repertoire for said antibody. A method of obtaining human antibodies using inter alfa single cell RT-PCR is described for example in the international application WO2008/110372, the disclosure content of which is incorporated herein by reference, in particular the Supplementary Methods section and Example 2. As used herein, the terms "cDNA" and "mRNA" encompass all forms of nucleic acid, including but not limited to genomic DNA, cDNA, and mRNA. Cloning and heterologous expression of the antibody or antibody fragment can be performed using conventional techniques of molecular biology and recombinant DNA, which are within the skill of the art (Wrammert et al., Nature 453 (2008), 667-671 and Meijer et al., 2006 J. Mol. Bio. 358 (2006), 764-772). Such techniques are explained fully in the literature, for example in Sambrook, 1989 Molecular Cloning; A Laboratory Manual, Second Edition. For retrieval of VH/VL sequences and expression the method of Tiller et al., in J. Immunol. Methods 329 (2008), 112-124 can be used. Any appropriate host cell for expressing the recombinant human antibody may be used, e.g., a yeast, a plant cell or an animal cell. Preferably, mammalian host cells such CHO cells and HEK cells are used; see also, e.g., European patent EP 1 974 020 B1 in sections [0164] to [0171] the disclosure content of which is incorporated herein by reference.

In one embodiment the constant region of the antibody of the present invention or part thereof, in particular the CH2 and/or CH3 domain but optionally also the CH1 domain is heterologous to the variable region of the native human monoclonal antibody isolated in accordance with the method of the present invention. In this context, the heterologous constant region(s) are preferably of human origin in case of therapeutic applications of the antibody of the present invention but could also be of for example rodent origin in case of animal studies.

In one embodiment of the method of the present invention, the antigen is selected from the group consisting of extracellular proteins and proteins, polysaccharides, lipopolyproteins and lipopolysaccharides, which are secreted, associated or attached to a membrane or transmembranous. However, in principle the method of the present invention is capable of providing autoantibodies against any desired antigen. This is because subjects preferably used in accordance with the invention, i.e. those who suffer from an autoimmune disorder and/or whose impaired central and/or peripheral tolerance or loss of self-tolerance is caused by a particular genotype, i.e. a monogenic autoimmune disorder due to the general responsiveness of their humoral immune response on the one hand and their exposure to different internal and external stimuli and conditions, respectively, comprising predisposition for an inherited disorder, toxins, infections, age-related disorders and the like on the other hand provide a pool of autoantibodies ranging from autoantibodies common to most if not all subjects to autoantibodies which are specific for an individual disease or condition. For autoantibodies commonly found in the pool of samples in one embodiment of the method of the present invention the antigen is selected from the group consisting of leukotrienes, lymphokines, cytokines, interleukins, interferons and chemokines.

Hence, suitability of the method of the present invention for the isolation of human monoclonal antibodies specific for and capable of neutralizing interleukin-17A (IL-17A), interleukin-17F (IL-17F) or interleukin-22 (IL-22) from memory B cells obtained from patients with Autoimmune polyendocrinopathy syndrome type 1 (APS-1) has been proven and is disclosed in applicant's co-pending international application PCT/EP2013/050024 "Method of providing monoclonal auto-antibodies with desired specificity" filed on Jan. 2, 2013, the disclosure content of which is incorporated herein by reference.

The isolated antibodies of the present invention may of course not be applied as such to a patient, but usually have to be pharmaceutically formulated to ensure, e.g., their stability, acceptability and bioavailability in the patient. Therefore, in one embodiment, the method of the present invention further comprises the step of admixing the isolated monoclonal antibody with a pharmaceutically acceptable carrier. A thorough discussion of pharmaceutically acceptable carriers is available in Remington's Pharmaceutical Sciences (Mack Publishing Company, N.J. 1991) and in Gennaro (2000) Remington: The Science and Practice of Pharmacy, 20th edition, ISBN: 0683306472. Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain agents commonly used in pharmaceutical formulations, such as suspending, preservative, stabilizing and/or dispersing agents. Alternatively, the antibody molecule may be in dry form, for reconstitution before use with an appropriate sterile liquid. Once formulated, the compositions can be administered directly to the subject. It is preferred that the compositions are adapted for administration to human subjects. The pharmaceutical compositions may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes.

The antibodies of the present invention or fragments thereof may be directly used as a therapeutic agent. However, in one embodiment the antibody or antigen-binding fragment which is provided by the present invention, is detectably labeled or attached to a drug, for example wherein the detectable label is selected from the group consisting of an enzyme, a radioisotope, a fluorophore and a heavy metal. Labeled antibodies or antigen-binding fragments of the present invention may be used to detect specific targets in vivo or in vitro including "immunochemistry/immunolabelling" like assays in vitro. In vivo they may be used in a manner similar to nuclear medicine imaging techniques to detect tissues, cells, or other material expressing the antigen of interest. Labels, their use in diagnostics and their coupling to the binding molecules of the present invention are known to the person skilled in the art.

Hence, the present invention also relates to a method of preparing an antibody or antigen binding portion thereof for pharmaceutical use or as target for therapeutic intervention, comprising the steps of any of the above-described methods of the present invention and illustrated in FIGS. 1 and 6, optionally wherein the antibody or binding fragment thereof is detectably labeled or attached to a functional domain or drug, preferably wherein the detectable label is selected from the group consisting of an enzyme, radioisotope, a fluorophore and a heavy metal.

The above disclosure generally describes the present invention. Unless otherwise stated, a term as used herein is given the definition as provided in the *Oxford Dictionary of Biochemistry and Molecular Biology*, Oxford University Press, 1997, revised 2000 and reprinted 2003, ISBN 0 19 850673 2. Several documents are cited throughout the text of this specification. Full bibliographic citations may be found at the end of the specification immediately preceding the claims. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

EXAMPLES

The Examples which follow and corresponding Figures further illustrate the invention, but should not be construed to limit the scope of the invention in any way. Detailed descriptions of conventional methods, such as those employed herein can be found in the cited literature.

The practice of the present invention will employ, unless otherwise indicated, conventional techniques of cell biology, cell culture, molecular biology, transgenic biology, microbiology, recombinant DNA, and immunology, which are within the skill of the art. Methods in molecular genetics and genetic engineering are described generally in the current editions of Molecular Cloning: A Laboratory Manual, (Sambrook et al., (1989) *Molecular Cloning: A Laboratory Manual,* 2nd ed., Cold Spring Harbor Laboratory Press); *DNA Cloning,* Volumes I and II (Glover ed., 1985); *Oligonucleotide Synthesis* (Gait ed., 1984); *Nucleic Acid Hybridization* (Hames and Higgins eds. 1984); *Transcription And Translation* (Hames and Higgins eds. 1984); *Culture Of Animal Cells* (Freshney and Alan, Liss, Inc., 1987); *Gene Transfer Vectors for Mammalian Cells* (Miller and Calos, eds.); *Current Protocols in Molecular Biology and Short Protocols in Molecular Biology,* 3rd Edition (Ausubel et al., eds.); and *Recombinant DNA Methodology* (Wu, ed., Academic Press). *Gene Transfer Vectors For Mammalian Cells* (Miller and Calos, eds., 1987, Cold Spring Harbor Laboratory); *Methods In Enzymology*, Vols. 154 and 155 (Wu et al., eds.); *Immobilized Cells And Enzymes* (IRL Press, 1986); *Perbal, A Practical Guide To Molecular Cloning* (1984); the treatise, *Methods In Enzymology* (Academic Press, Inc., N.Y.); *Immunochemical Methods In Cell And Molecular Biology* (Mayer and Walker, eds., Academic Press, London, 1987); *Handbook Of Experimental Immunology*, Volumes I-IV (Weir and Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., *Curr. Opin. Biotechnol.* 8 (1997), 148); Serum-free Media (Kitano, *Biotechnology* 17 (1991), 73); Large Scale Mammalian Cell Culture (*Curr. Opin. Biotechnol.* 2 (1991), 375); and Suspension Culture of Mammalian Cells (Birch et al., *Bioprocess Technol.* 19 (1990), 251.

Material and Methods

Short Term Culture of Memory B Cell Polyclonally Stimulated

Memory B cells were isolated from human peripheral blood mononuclear cells derived from the peripheral blood of voluntary Finnish patients with Autoimmune polyendocrinopathy candidiasis ectodermal dystrophy (APECED, OMIM 240300), also called autoimmune polyendocrine syndrome type 1 (APS1) and fro healthy volunteers with a one step protocol using phycoerythrin-conjugated mAb anti-human IgD, APC-conjugated mAbs anti-human IgM, CD3, CD56, CD8 and FITC-conjugated mAb anti human CD22 (Becton Dickinson, Basel, Switzerland). Cell sorting was carried out using a MoFlo XDP cell sorter (Beckman Coulter). CD22-positive- and CD3-, CD56-, CD8-, IgM-, IgD-negative B cells were then polyclonally stimulated with the early functions of EBV (Tsuchiyama et al., Hum Antibodies. 8 (1997), 43-47) by incubating them with supernatant obtained from B95-8 cells ((maximum up to 50% B95-8 supernatant in a total volume of 2 ml of RPMI 1640 with GlutaMAX™-I supplemented with 1% sodium pyruvate, 1% non-essential amino acids, 50 U/ml Penicillin/Streptomycin, 50 uM b-mercaptoethanol, 10% Fetal Bovine Serum). After 3 to 5 hours (preferably 3 hours 30 minutes) incubation, EBV is diluted out by diluting memory B cells in appropriate volume of IMDM medium with L-Glutamine, supplemented with 1% sodium pyruvate, 1% non-essential amino acids, 50 U/ml Penicillin/Streptomycin, 50 uM b-mercaptoethanol, 10% Fetal Bovine Serum, and CpG 2006 (2.5 ug/ml) (in some experiments 30 ug/ml transferrin (Life Technologies) has been supplemented as well) and irradiated feeder PBMCs prepared from healthy donors to seed 10 memory B cells and 30,000 PBMC feeder cells per well of 96-well U-bottom plates in 200 ul. The dilution of EBV supernatant is typically >1:800 (i.e. 0.125%). Alternatively, EBV is washed out by centrifuging cells and discarding supernatants. In some cases cells were plated with 50,000 PBMC feeder cells per well.

Culture conditions that support human IgG secretion were evaluated at day 9-12 by determining the percentage of cultures with human IgG levels in supernatants diluted 1:9 that are above the average between the three highest and three lowest cultures. For each culture condition tested, supernatants from two plates were measured by ELISA.

After 8-14 days of culture the conditioned medium of memory B cell culture was screened for the presence of antigen of interest-specific (e.g., IL-17, IL-22) antibodies by ELISA. In this context, the same culture supernatant can be tested on several different antigens (possibly all the antigens against which serum reactivity was observed for the biological sample, e.g. in protoarray. For example, 96 well microplates (Costar, USA) are coated with the antigen of interest. Plates are washed with PBS-T and blocked 1 h at room temperature with PBS containing 2% BSA (Sigma, Buchs, Switzerland). Patient sera, B cell conditioned medium, or recombinant antibody preparations are incubated for 2 h at room temperature. Binding of human IgG to the antigen of interest can be determined using a horseradish peroxidase conjugated goat anti human IgG Fc-gamma-specific antibody (Jackson ImmunoResearch, Europe Ltd., Cambridgeshire, UK) followed by measurement of the HRP activity using a TMB substrate solution (TMB, Sigma, Buchs, Switzerland).

Example 1: Isolation of Peripheral Blood Mononuclear Cells (PBMC) from APECED/APS-1 Patients As starting material for the isolation cloning of fully human antibodies, human lymphocytes were used obtained from the peripheral blood of 23 voluntary Finnish patients with Autoimmune polyendocrinopathy candidiasis ectodermal dystrophy (APECED, OMIM 240300), also called autoimmune polyendocrine syndrome type 1 (APS1). These volunteers were recruited for the blood donation through the Finnish APECED and Addison patient association. All patients gave their written informed consent and the study has been approved by the Medicine Ethical Review Board of the Joint Authority of Helsinki and Uusimaa hospital district. APECED is an autosomal recessive disorder caused by mutations in the AIRE (autoimmune regulator) gene, located on chromosome 21 (21q22.3) and APECED is prevalent in Finland (1/25,000) because of a founder effect. APECED patients present with various endocrine autoimmune dysfunctions including mainly adrenal failure and hypoparathyroidism, but also variously hypogonadism, diabetes mellitus, thyroiditis and hypophysitis. Other main symptoms are chronic mucocutaneous candidiasis, alopecia and vitiligo (see also supra). Since a strong correlation between the antigen-specific IgG levels in the serum and the frequency of antigen-specific B cells in the memory pool of peripheral blood mononuclear cells has been reported (Bernasconi et al. 2002, Lanzavecchia et al. 2006), patient sera were first screened for the presence of autoantibodies against the proteins of interest (like IFN, IL-17, IL-22) and then those APECED cases with high titer (>1:5000) were selected for peripheral blood mononuclear cell (PBMC) isolation as follows. Heparinized peripheral blood was obtained and diluted with two volumes of 1×PBS at RT, and the cells were overlayed on Lympholyte H, centrifuged at 2000 rpm (805 rcf) at RT for 20 minutes. The cells were harvested at interphase, mixed in washing buffer fill, centrifuged at 1,500 rpm (453 rcf) for 15 min at 4° C. and resuspended by gentle flicking, with 10 ml WB. Thereinafter the cells were centrifuged at 1,000 rpm (201 rcf), 10 min at 4° C. and washed once more with WB. The cells were then resuspended gently in appropriate volume of FBS on ice. FBS was added to adjust volume to have 20 mio/ml whereafter 1 volume of freezing medium (80% FBS (Hyclone, Thermo Scientific and 20% DMSO, #154938, Sigma) was slowly added while stirring, resuspended and aliquoted into cryovials kept on ice. The cryovials were placed in Mr. Frosty box and transferred to −80° C. freezer for a maximum of 5 days before freezing in liquid nitrogen or further processing as described in Examples 2-4. Alternatively, the cryovials were stored in liquid nitrogen.

Figure 2:
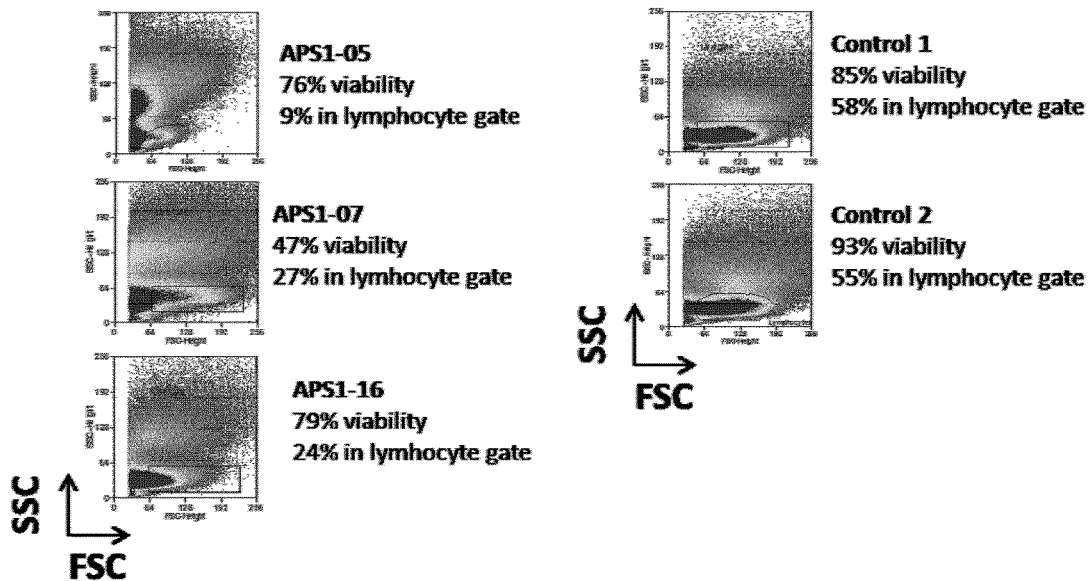
FIG. 2: Analysis of frozen PBMC samples from APS1 patients and healthy donor control. PBMC were isolated from fresh blood donations from three APS1 patients (APS1-05, APS1-07, APS1-16) and two healthy donors (Control 1, Control 2), and frozen in liquid nitrogen. Cells were thawed and analyzed for viability by counting with trypan blue and analyzing FSC/SSC by flow cytometry. Viability of thawed PBMC from APS1 patients varied from 47% to 87% whereas for control samples it was consistently above 71% (81% average). FSC/SSC also shows a reduced percentage of cells from thawed PBMC from APS1 patients in the lymphocyte gate.

Example 2: Reduced Viability of Thawed PBMC and Reduced Percentage of Cells from Thawed PBMC from APS1 Patients in the Lymphocyte Gate Aliquots of 1 ml frozen PBMCs prepared as in Example 1, were thawed in water bath at 37° C., overlayed on 10 ml ice cold RPMI 1640 complete medium and gently mixed. An aliquot of cells was taken for counting cells with trypan blue, while remaining cells were centrifuged. Supernatant was discarded and cells processed as indicated in the material and methods for the isolation of memory B cells. FIG. 2 shows FCS/SSC dot plots of PBMCs from APS1 patients and healthy donor controls stained for sorting memory B cells (MoFlow sorter). Viability of thawed PBMC from APS1 patients varied from 47% to 87% whereas for control samples it was consistently above 71% (81% average). FSC/SSC also shows a reduced percentage of cells from thawed PBMC from APS1 patients in the lymphocyte gate. These data indicate that cells from APS1 patients are fragile and particularly sensitive to freezing and thawing.

Example 3: Ig Production by Short Term Cultures of Memory B Cells Activated with CpG after Removal of EBV Previous attempts at the cellular cloning of identified tumor antigen-specific EBV-transformed human memory B cells had not been successful (WO 2008/110373 A1). Similarly, during experiments performed within the scope of the present invention it turned out that previous methods aiming at B cell immortalization for providing a B cell clone producing the antibody of interest such as those described in international application WO 2004/076677 do not work quite well if at all for B cells of APS1 patients, suggesting that the majority of cells are not transformed and not immortalized. Therefore, it was decided to attempt isolation of antibodies of desired antigen specificity by cloning immunoglobulin genes from single cells sorted from short-term oligoclonal cultures (1-2 weeks) rather than by cellular cloning of immortalized B cells. With the aim of inducing secretion of antibodies in detectable amounts to allow appropriate screening assays for early (within 2 weeks) selection of oligoclonal cultures producing the antibody of interest, attempts were made to improve B cell culture conditions. Further, transferrin was found to be the only essential exogenous factor to support growth of B lymphoblasts immortalized with EBV (Gordon, J Exp Med 159 (1984): 1554-1559). Based on this it was tried to improve protocols using EBV and CpG by incubating cells with EBV for a limited time and then either diluting it out by plating cells in medium containing CpG but not EBV (dilute out), or eliminating EBV through cell wash before plating in medium with containing CpG but not EBV (wash out). Further, IgG production by cells plated in different media (RPMI 1640 or IMDM) in the presence or absence of transferrin was investigated. Specific procedures and culture conditions are detailed in material and methods and in the legend of FIGS. 3, 4 and 5. Experiments were performed with healthy donor control cells (FIGS. 3 and 4) and with cells from one APS1 patient (FIG. 5).

As shown in FIG. 3, limited incubation of cells with EBV before plating in medium without EBV supplemented with CpG gave better results than exposing cells simultaneously to EBV and CpG. In fact, almost two-fold higher percentage of IgG producing cultures was observed when EBV was diluted or washed out after 4 hours 30 minutes and cells were plated in IMDM medium supplemented with tranferrin and CpG (#2 and 3) compared to cells plated directly in RPMI supplemented with EBV and CpG. Further, similar results were obtained if EBV is diluted out or completely eliminated by centrifuging cells and discarding supernatants (compare #2 and 3). Additionally, cultures plated in IMDM medium did better than cultures plated in RPMI medium (compare #6 and 7) and rather than being beneficial (as it would be expected if B cells would be transformed by EBV at this stage) transferrin proved to be detrimental (compare #4 and 5, and #7 and 8).

The results above were confirmed in experiments shown in FIG. 4, aimed at direct comparison of the method of the present invention (#3-5) with the procedure described to immortalize cells as described in Traggiai et al. Nat. Med. 2004 and EP 1 597 280 B1, i.e. plating cells in medium with EBV (20% based on Example 8 of EP 1 597 280 B1)+CpG (#1), or 6 h with 50% EBV before plating in medium with EBV+CpG (based on Example 3 of EP 1 597 280 B1) (#2). Again, almost half of IgG producing cultures were obtained when cells were plated in medium with 20% EBV and CpG compared to cultures exposed only temporary to EBV and then stimulated with CpG in the absence of EBV (compare #1-2 with 3-5). Also in this case, if anything eliminating completely EBV (wash out) was better than diluting (dilute out) (#5 and 4).

In the experiment shown in FIG. 5 cells from patient APS1-07 were used to further compare the extent of IgG secretion by cells treated according to the EBV immortalization procedure as taught in EP 1 597 280 B1, Example 8) (#1), or as taught in Traggiai et al) (#2), by plating cells in medium supplemented with 2.5 ug/ml CpG and 20% or 30% EBV respectively, and by oligoclonal cultures generated according to the method of the present invention i.e. incubation with EBV for a limited time (3.5 hours) and diluting or washing out EBV (#4 and 5, respectively) before providing the second polyclonal stimulator CpG. Also in this case limited exposure to EBV led to a higher percentage of IgG producing cultures (#3-4 and 1-2).

Example 4: Isolation of Human Antibodies of Desired Specificity by Molecular Cloning Memory B cells were isolated from PBMC derived from the peripheral blood of voluntary Finnish APECD patients and polyclonally stimulated with EBV and then activated with CpG in short term cultures to allow secretion of antibodies as illustrated in FIG. 6 and described in material and methods and in Example 3. After 7 to 14 days, culture supernatants are screened for the presence of antibodies specific for the target of interest (e.g. IL17, IL-22), for example using standard ELISA assay. Using a cell sorter, single cells from IL-17/IL-22-reactive oligoclonal memory B cell short-term cultures (one or two weeks) are deposited into a 96 well PCR plate, containing first strand buffer (Invitrogen, LuBioScience, Switzerland). cDNA is prepared using Random hexamer primer (Invitrogen, LuBioScience, Switzerland). PCR amplification of immunoglobulin heavy and light chain variable regions is performed according to standard protocols (Wardemann et al., Science 301, 2003, 1374-1377). Immunoglobulin heavy and light chain variable regions are amplified using a nested PCR approach. 1st round PCR is performed with primers specific for the IgG constant region and primer mixes specific for all signal peptides of heavy and light chain Ig variable region families (Wardemann et al., *Science* 301, 2003, 1374-1377). Subsequently, nested PCR is performed using primer mixes specific for the immunoglobulin J-regions and the 5' region of framework 1 of heavy and light chain Ig variable region families. Sequence analysis is carried out to identify the individual antibody clones present in the selected B-cell culture. Subsequently, the Ig-variable heavy- and light regions of each antibody clone are cloned into expression vectors providing the constant regions of human IgG1, human Ig-Kappa or human Ig-Lambda. Upon co-transfection of the Ig-heavy- and light expression vectors into HEK 293 cells the antibody clones are produced. Identification of the antibody clone presumably responsible for the IL-17/IL-22-reactivity of the parental B cell culture is performed upon re-screening of the recombinant antibody clones in IL-17/IL-22- and control ELISA.

In order to identify and to correct primer encoded sequence mismatches in the Ig-variable region a further PCR amplification using a semi-nested protocol is performed with 2 primer pairs specific for a conserved region of the Ig-heavy- and light chain constant regions as 3'-primers and primer mixes specific for the Ig-signal peptides as 5'-primers. PCR products are cloned into TOPO™ vector (Invitrogen, LuBioScience, Lucerne, Switzerland). Sequence determination of the complete Ig-variable region is carried out and the information is used to design specific primers for the cloning of the authentic human antibody sequence into antibody expression vectors. This approach allows the identification of the complete antibody sequence of the Ig-variable region as it occurred in the patient. This sequence is used for recombinant production of these antibodies which are then used in the subsequent characterization steps.

Example 5: Antibody Production and Purification

Transient gene expression of human antibodies is achieved upon transfection of antibody expression vectors into 293-T human embryonic kidney cells or Chinese Hamster Ovary cells (CHO) using the Polyethylenimine Transfection method (PEI, Polyscience Warrington, USA). After transfection cells are cultured in serum free medium (OPTI-MEM I supplemented with GlutaMAX-I Gibco). Supernatants are collected after 3-6 days of culture and IgG is purified using protein A columns (GE HealthCare, Sweden) on a fast protein liquid chromatography device (FPLC) (GE HealthCare, Sweden).

The invention claimed is:

1. A method of producing a human antibody or binding fragment thereof with desired specificity characterized by isolating B cells from short term oligoclonal cultures of activated B cells that secrete antibodies of IgG isotype comprising:
    (a) selecting memory B cells that express antibodies against a protein of interest from one or more biological samples derived from a subject suffering from an autoimmune disease, whose sera is screened for the presence of auto-antibodies against a protein of interest, on the basis of the expression of at least one of CD22 cell-surface membrane marker and antigen binding;
    (b) stimulating the selected cells for about three to five hours with a first polyclonal B cell activator which is Epstein-Barr virus (EBV) under cell culture conditions and in the absence of a second polyclonal B cell activator;
    (c) separating the cells from said activator;
    (d) activating the stimulated cells with a second polyclonal B cell activator which is a CpG-based oligonucleotide under cell culture conditions; and,
    (e) screening the activated cells to identify cells that express IgG isotype antibodies of interest, wherein the culture conditions of step (d) do not comprise a cytokine.

2. The method of claim 1, wherein the culture conditions in step (b) do not comprise a cytokine.

3. The method of claim 1, wherein in step (c) the first polyclonal activator is removed by diluting or washing out.

4. The method of claim 1, wherein in step (d) the transferred new selected cells are exposed to the second polyclonal activator for about eight to fourteen days.

5. The method of claim 1, wherein in at least one of step (d) and (e) the cells are cultured under oligoclonal conditions with about ten cells per well in eight to fourteen day cultures.

6. The method of claim 1, wherein the method comprises
    (i) obtaining mRNA from bulk or single B cells sorted from short term oligoclonal cultures of activated B cells secreting the antibody of the invention;
    (ii) obtaining cDNA from the mRNA of step (i);
    (iii) using a primer extension reaction to amplify from said cDNA the gene repertoire corresponding to the heavy chains (HC) and the light chains (LC) and optionally constant domain of said antibodies;
    (iv) using said repertoire to express said antibody or an antigen-binding fragment thereof in a host cell;
    (v) identifying the antibody clone presumably responsible for the reactivity of the parental B cell culture; and
    (vi) isolating the monoclonal antibody or an antigen-binding fragment thereof.

7. The method of claim 6, wherein the host cell is an animal cell.

8. The method of claim 6, wherein the DNA is manipulated between steps (iii) and (iv) in a manner selected from the group consisting of introducing at least one restriction site, changing codon usage, introducing coding sequences for functional domains or peptide linkers; adding or optimizing transcription or translation regulatory sequences, and combinations thereof.

9. The method of claim 1, wherein the protein of interest is selected from the group consisting of extracellular proteins, polysaccharides, lipopolyproteins and lipopolysaccharides, which are secreted, associated or attached to a membrane or transmembranous.

10. The method of claim 9, wherein the antigen is selected from the group consisting of leukotrienes, lymphokines, cytokines, interleukins, interferons and chemokines.

11. The method of claim 1 further comprising the step of admixing the isolated monoclonal antibody or antigen binding fragment thereof with a pharmaceutically acceptable carrier.

12. The method of claim 1, wherein the antibody or binding fragment thereof is attached to a functional domain or drug, or a detectable label selected from the group consisting of an enzyme, radioisotope, a fluorophore and a heavy metal.

13. The method of claim 1, wherein the B cells are depleted in IgM and IgD isotypes.

14. The method of claim 1, further comprising:
    single-cell harvesting of oligoclonal cultures producing the antibody of interest; and, sequencing or cloning the cDNA of at least one of the variable light, the heavy chain regions and the constant region of the antibody of interest.

* * * * *